United States Patent [19]
Andersen

[11] Patent Number: 5,609,702
[45] Date of Patent: Mar. 11, 1997

[54] METHOD AND ARRANGEMENT FOR MUTUALLY BONDING MOVING MATERIAL WEBS, AND ABSORBENT ARTICLES THAT INCLUDE MATERIAL LAYERS MUTUALLY BONDED IN ACCORDANCE WITH THE METHOD

[75] Inventor: Verner E. Andersen, Mölnlycke, Sweden

[73] Assignee: Molnlycke AB, Gothenburg, Sweden

[21] Appl. No.: 411,809

[22] PCT Filed: Oct. 11, 1993

[86] PCT No.: PCT/SE93/00827

§ 371 Date: Apr. 10, 1995

§ 102(e) Date: Apr. 10, 1995

[87] PCT Pub. No.: WO94/08789

PCT Pub. Date: Apr. 28, 1994

[30] Foreign Application Priority Data

Oct. 12, 1992 [SE] Sweden ................................. 9202993

[51] Int. Cl.⁶ ............................................. B32B 31/16
[52] U.S. Cl. .................... 156/73.1; 156/183; 156/292; 156/308.4; 156/553; 156/580.2
[58] Field of Search ........................... 156/73.1, 73.2, 156/73.4, 160, 163, 164, 183, 229, 290, 324, 494, 495, 553, 555, 580.1, 580.2, 292, 324.4; 100/93 RP

[56] References Cited

U.S. PATENT DOCUMENTS

| | | | |
|---|---|---|---|
| 4,311,540 | 1/1982 | Hill | 156/73.1 |
| 4,610,743 | 9/1986 | Salmeen et al. | 156/183 |
| 4,720,415 | 1/1988 | Vander Wielen et al. | 428/152 |
| 4,854,984 | 8/1989 | Ball et al. | 156/73.5 |
| 4,919,738 | 4/1990 | Ball et al. | 156/73.5 |
| 5,370,764 | 12/1994 | Alikhan | 156/553 |

FOREIGN PATENT DOCUMENTS

| | | |
|---|---|---|
| 0264676A1 | 4/1988 | European Pat. Off. . |
| 0295957A1 | 12/1988 | European Pat. Off. . |
| 0409315A1 | 1/1991 | European Pat. Off. . |
| 60-155797 | of 1984 | Japan . |
| 1094166 | 12/1967 | United Kingdom . |
| 2012673 | 8/1979 | United Kingdom . |
| 2103998 | 3/1983 | United Kingdom . |

OTHER PUBLICATIONS

WPI Access No. 85-239665/39 (Abstract) 1985.

*Primary Examiner*—James Sells
*Attorney, Agent, or Firm*—Burns, Doane, Swecker & Mathis LLP

[57] ABSTRACT

The present invention relates to a method for mutually bonding at least two moving continuous material webs of material (1,5) to form a laminate (12) which includes at least one puckered material layer. A first and second web (1,5) are advanced at different speeds ($V_1$, $V_2$) to a web bonding means (4) in which the webs are mutually bonded and the resultant laminate (12) is further advanced at the lower speed ($V_2$). Because of the difference in speed between the two webs, that web (1) which moves at the higher speed ($V_1$) at the web bonding moment is puckered while the other web (5) remains smooth. The invention also relates to an arrangement for mutually bonding two material webs (1,5) in accordance with the method, and to an absorbent article (17) which includes a liquid-receiving outer layer (20) which contains at least one puckered, first liquid-permeable layer (21) and at least one smooth, second liquid-permeable layer (22).

11 Claims, 2 Drawing Sheets

METHOD AND ARRANGEMENT FOR MUTUALLY BONDING MOVING MATERIAL WEBS, AND ABSORBENT ARTICLES THAT INCLUDE MATERIAL LAYERS MUTUALLY BONDED IN ACCORDANCE WITH THE METHOD

BACKGROUND OF THE INVENTION

The present invention relates to a method and to an arrangement for mutually bonding at least two moving continuous webs of material. The invention also relates to a disposable absorbent article, such as a diaper, a sanitary napkin, an incontinence guard or the like which includes an absorbent pad, a liquid-impermeable layer on one side of the pad and a liquid-permeable, liquid-receiving outer layer on the other side of the pad, said outer layer including at least two mutually bonded liquid-permeable layers.

Methods for mutually bonding two or more moving material webs to form an essentially smooth laminate are known in the art. According to one such known method, the material webs are thermobonded between two heated, rotating rolls. According to another method, a binding agent is applied to at least one of the webs, whereafter the webs are combined and bonded to one another, for instance by passing the webs between two rolls. Another known method involves laminating two material webs with the aid of ultrasonic welding techniques. A prerequisite for both thermobonding and ultrasonic welding is that at least one of the webs includes weldable material. In these cases, the webs are comprised, for instance, of non-woven fabric comprising fibres of, for instance, polyethylene, polypropylene, polyester or the like. Webs of thermoplastic films are another example of such material webs.

The European Patent Application EP-A-0 409 315 teaches a method of producing a laminate which includes at least one corrugated laminate layer. Two laminate layers, of which at least one has corrugations in the movement direction of the layer, are passed through the nip of two rolls of which at least one has a plurality of peripheral grooves in which the corrugations are intended to fit while the layers are mutually bonded in regions located between the corrugations, i.e. in regions corresponding to the spaces between the grooves in the roll or rolls. According to this known laminating method, it is important that the corrugations are not displaced laterally so as to leave the grooves, i.e. to lie completely or partially between the grooves in the roll or rolls. If this should happen, wrinkles are formed in the laminate and which is said to be unsatisfactory.

It is also known from the so-called MICREX process, proposed by Micrex® Corporation, to microcrêpe material webs that are comprised, for instance, of non-woven fabric. This process, however, is not concerned with mutually joining two material webs, and the microcrêping process is carried out on a single layer, or on a laminate, comprised for instance of non-woven fabric. Microcrêping can be likened to microscopic wrinkling of the material web transversely to its movement direction. However, the durability of the wrinkles in the web in a continued manufacturing process is highly uncertain. In one diaper manufacturing process for instance, the web is subjected to significant tensile forces in the process direction of the web and the diaper manufacturing machine. Since the wrinkles are not permanently set, there is a serious risk that the wrinkles will be smoothed-out when the web is subjected to forces in its longitudinal direction. Furthermore, if the microcrêped material webs are rolled-up on a rack after the microcrêping process and before being used in the diaper manufacturing process, the wrinkles may be influenced unfavourably, e.g. may be smoothed-out and disappear.

OBJECT AND SUMMARY

The present invention relates to a method which will enable moving webs of material to be mutually bonded quickly and simply, in a manner such that at least one of the webs will be permanently puckered while at least one of said webs will remain essentially smooth. According to the invention, this is achieved with a method of the kind defined in the introduction which further comprises the steps of advancing a first web of material from a first depot or store at a first speed, advancing a second web of material from a second depot or store at a second speed which is lower than the first speed, bringing the first web and the second web together and mutually bonding said webs to form a laminate with the aid of a web bonding arrangement while maintaining the speed difference between the first web and the second web, wherein said first web is puckered upon entry into the web bonding arrangement as a result of the higher speed of said first web in relation to the speed of the second web at the web bonding moment, while the second web remains essentially smooth, and advancing the laminate from the web bonding arrangement at a speed which is equal to the second and lower speed. The invention also relates to an arrangement for carrying out the method.

Earlier known web bonding methods have either been intended to provide the smoothest possible laminate, i.e. have been intended to avoid puckering of the webs in the laminating process, or, as in the case of EPA-0 409 315, the intention has been to preform corrugations and to carefully avoid wrinkling of the corrugations at the web-bonding moment. An intention of the present invention is to form folds or wrinkles at the actual web-bonding moment. The puckers thus formed in one of said webs are also made permanent, because the web is bonded to another, smooth web at points and/or curves between the folds or wrinkles. Thus, it is impossible to smooth-out the wrinkles by applying a tensile force to the laminate in the direction of its longitudinal axis. Smoothing-out of the wrinkles is prevented by the smooth web layer and the wrinkles will therewith be permanent.

Another object of the invention is to provide an absorbent article of the kind defined in the introduction which will allow liquid to quickly pass therethrough and which has a low re-wetting tendency. This is achieved by the fact that at least a first of said liquid-permeable layers is puckered or wrinkled and that a second of said liquid-permeable layers is essentially smooth.

A liquid-receiving outer layer according to the invention is able to receive a large volume of liquid, because the first liquid-permeable layer is puckered. The first layer thus exhibits a large number of troughs and peaks which considerably increase the volume of the liquid-receiving outer layer in comparison with a perfectly smooth liquid-receiving outer layer.

Other features of the present invention and advantages afforded thereby will be evident from the following description and claims.

BRIEF DESCRIPTION OF THE DRAWINGS

The invention will now be described in more detail with reference to exemplifying embodiments thereof and also with reference to the accompanying drawings, in which.

DETAILED DESCRIPTION OF THE PREFERRED EMBODIMENTS

Figure 1:
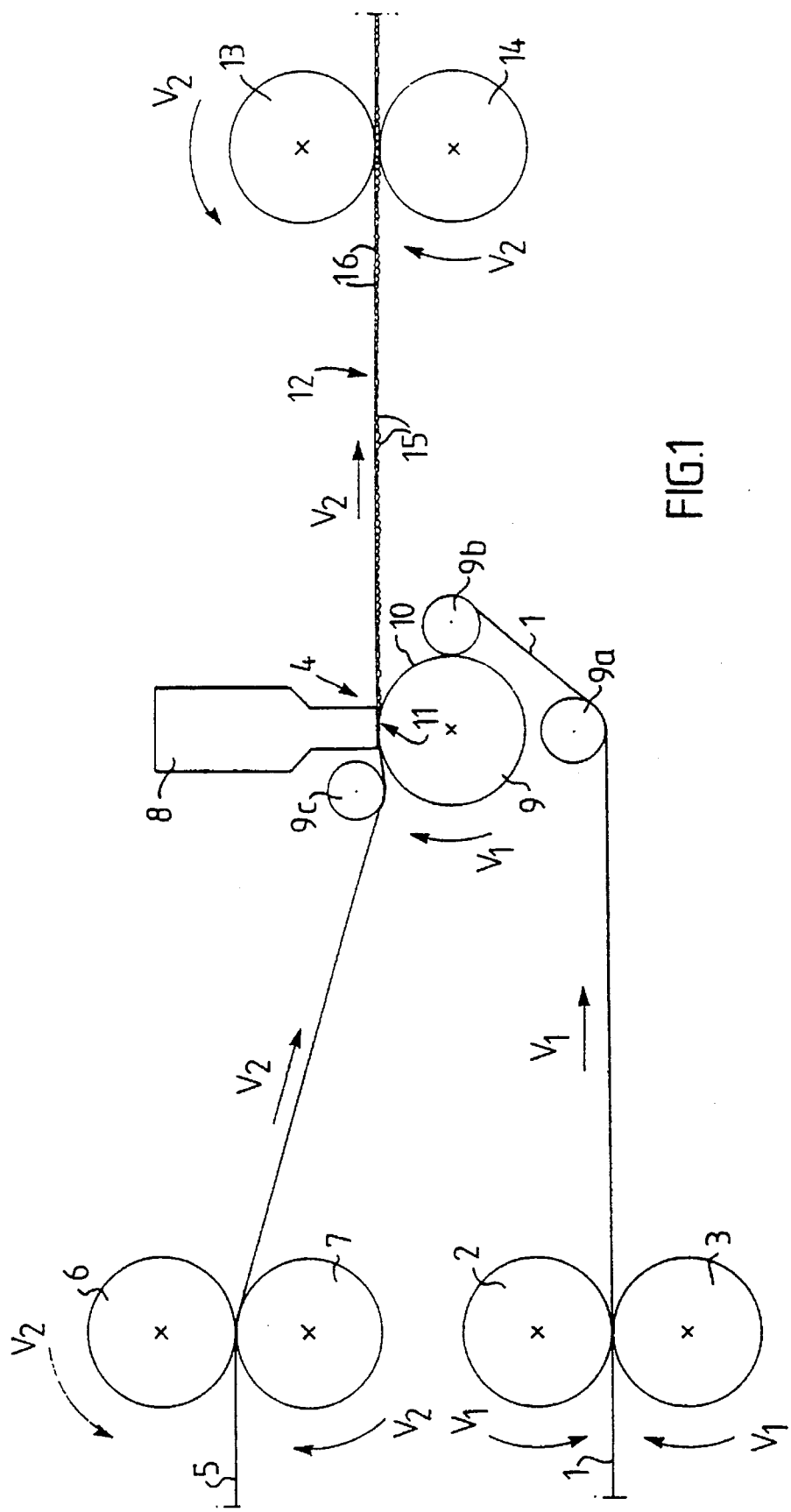
FIG. 1 illustrates schematically a method and an arrangement according to one embodiment of the invention.

As illustrated in FIG. 1, a first web of material 1 is advanced from a first depot or store (not shown) and in between two rotating rolls 2 and 3 whose peripheral speeds are equal to a first speed $V_1$. The first web 1 is thus advanced at said first speed $V_1$ to a web-bonding means 4, via guide rollers 9a, 9b. A second web of material 5 is advanced from a second depot or store (not shown) and in between two rotating rolls 6 and 7 whose peripheral speed is equal to a second speed $V_2$, and the second web 5 is then further advanced to the web-bonding means 4 via a guide roller 9c at said second speed $V_2$. The first speed $V_1$ is higher than the second speed $V_2$ and the speed of the first web 1 will thus be higher than the speed of the second web 5 as the two webs move through the web-bonding means 4. The web-bonding means 4 includes an ultrasonic horn 8 and a rotating counterpressure roll 9 whose peripheral speed corresponds to the first speed $V_1$. The horn 8 and the roll 9 define therebetween a nip 11 through which the two webs 1, 5 pass. The second web 5 will pass between the horn 8 and the first web 1 and the first web 1 will lie against the rotating counterpressure roll 9 as the two webs 1, 5 are mutually bonded to form a laminate 12. The ultrasonic horn 8 vibrates at a suitable frequency, for instance a frequency of 20 kHz or thereabove, and lies under pressure against the roll 9. Disposed on the roll 9 are a number of elements which stand out from the outer surface 10 of the roll, these elements being too small to be seen in the schematic view of FIG. 1. However, these elements are disposed in any suitable manner known to the skilled person, for instance in a discontinuous pattern of discrete spikes, elongated ribbons arranged essentially in the axial direction of the counterpressure roll, or like arrangements. The pattern may be regular or irregular and it may cover the whole of the outer surface 10 of the counterpressure roll or may solely cover parts thereof. The outwardly projecting elements function as local dollies or anvils in the formation of welded laminate parts as the first and the second webs 1, 5 pass through the nip 11 between the ultrasonic horn 8 and the counterpressure roll 9. The mutually welded first and second webs 1, 5 thus leave the web bonding arrangement 4 as a laminate 12 which then passes between two rotating rolls 13, 14 whose peripheral speeds are equal to the second speed $V_2$.

Figure 2:
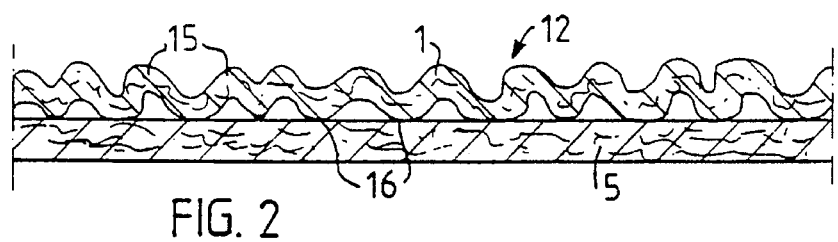
FIG. 2 is a longitudinal sectional view of part of a laminate constructed in accordance with the method illustrated in FIG. 1.

As the first web 1 passes through the nip 11 in the web-bonding arrangement 4 at a speed $V_1$ which is higher than the second speed $V_2$, this speed being the speed at which the second web 5 passes through the web-bonding means 4 and at which the laminate 12 leaves said arrangement 4, a given length of the first web 1 will be puckered or wrinkled as a result of the sudden transition from the higher speed $V_1$ upstream of the web bonding moment, to the lower speed $V_2$ downstream of said web-bonding moment. In other words, at the moment of mutually bonding the webs, there is an abrupt decrease in the speed of the first web 1 in the nip 11 without the trailing parts of the first web 1 that have still not yet reached the nip 11 experiencing the same reduction in speed. This additional forward feed of the first web 1 in comparison with the second web 5, which moves at said second speed $V_2$ during the whole of the process, results in the formation of transverse folds 15 in the first web 1. These folds 15 are permanently locked between the bonding regions 16 of the laminate 12. This will best be seen from FIG. 2. The choice of the speed differential between $V_1$ and $V_2$ will depend on the size of the folds desired, i.e. how much additional length of material shall be fed forward by the first web 1. Other factors which influence the choice of this difference in web speeds include the size of the outwardly projecting elements, i.e. their length extension, and the "contraction rate" of the webs. At small speed differences, no appreciable folding of the material will take place, and retardation of the faster moving first web will solely result in deformation in the plane of the web. Naturally, different materials have different resistances to deformation. Consequently, the speed difference $V_1-V_2$ must be greater than the "contraction rate" for each given material, so as to enable folds to be formed in the material web. Suitable conditions are achieved when $V_1$ is at least 40% higher than $V_2$, to ensure that said condition will be satisfactorily fulfilled. For instance, $V_1$ may be approximately twice as high as $V_2$, although speed differences of 150%, 200% or still greater are conceivable. In some cases, the counterpressure roll 9 shown in FIG. 1 may have a peripheral speed which exceeds $V_1$.

In the case of the embodiment illustrated in FIG. 1, the first web 1 may have the same width as the second web 5 or may be narrower when desiring a laminate 12 that has folds solely over a part of its width. When the first web 1 is narrower than the second web 5, the first web 1 may be either centred in relation to the imaginary, longitudinally extending symmetry axis of the web 5 or may be offset laterally in either direction. In this latter case, it is also conceivable for a third web of material to move along side the first web 1 and slightly displaced laterally therefrom, up to the web-bonding means 4. In this case, the total width of the first and the third webs will be smaller than the width of the smooth, second web. This enables the laterally separated parts of the bonded web to be provided with folds. Naturally, it is conceivable to bond more than two narrow webs with the smooth web. For instance, it is possible to produce a laminate which exhibits strips of many, narrow puckered or folded layers. Naturally, any one of the webs forming the laminate 12 may, in turn, consist of a multi-layer laminate and thus need not necessarily be comprised of solely one single layer.

Examples of material webs which can be bonded together in accordance with the present invention include non-woven fabrics, for instance spun-bonded fabric and thermobonded fabric. Other weldable materials are also conceivable, such as thermoplastic films, which may also be perforated. It is also conceivable for only one of the webs to comprise weldable material. The other web or webs may, in this case, be comprised of tissue material, for instance.

As an alternative, a calendar may be used instead of the web-bonding means illustrated in FIG. 1. A calendar includes two counter-rotating, heated rolls or cylinders between which the webs are bonded together as they pass therebetween. One roll rotates at a peripheral speed corresponding to the first, higher speed $V_1$ and the second roll rotates at a peripheral speed corresponding to the second, lower speed $V_2$. The mutually bonded webs, i.e. the laminate, exiting from the rolls travels at the lower speed $V_2$. In the precise manner described with reference to FIG. 1, the first web will be puckered or folded in parts which lie upstream of the web-bonding site in the roll nip as a result of the abrupt change in speed in the web-bonding moment upon passage between the rolls. The second web remains smooth, similar to the second web of the FIG. 1 embodiment. Similar to the counterpressure roll 9, one of the calendar rolls has a discontinuously patterned surface.

A laminate produced in accordance with the inventive method is particularly suited for use as a liquid-receiving outer layer of a disposable absorbent article, such as a diaper, incontinence guard and the like. An incontinence guard 17 will now be described by way of an example of an inventive absorbent article, with reference to FIGS. 3 and 4.

The illustrated incontinence guard 17 includes an absorbent pad 18, a liquid-impermeable outer layer 19 on one side of the pad 18, and a liquid-receiving outer layer 20 on the other side of said pad. When the article is worn, the liquid-receiving outer layer 20 is intended to face towards the wearer. The liquid-receiving outer layer 20 includes a puckered, first liquid-permeable layer or sheet 21, and an essentially smooth, second liquid-permeable layer 22. The smooth, second liquid-permeable layer 22 is placed nearest the absorbent pad 18, while the puckered, first liquid-permeable layer 21 is placed on that side of the smooth, second layer 22 which is distal from the pad 18. The puckered, first liquid-permeable layer 21 presents a large number of folds or wrinkles which extend essentially in the longitudinal direction of the incontinence guard 17. The puckered, first layer 21 is bonded to the smooth, second layer 22 at a number of bonding regions 16 in the form of a large number of discrete binding points, for instance in the form of punctiform welds. The first liquid-permeable layer 21 and the second liquid-permeable layer 22 both include weldable material. These materials may be comprised, for instance, of non-woven fabric of the thermobond and/or spun-bond type. The two liquid-permeable layers 21, 22 may be comprised of different types of non-woven fabric or may be comprised mutually of the same kind of non-woven fabric, provided that the layers can be bonded together by thermobonds or welds, for instance by ultrasonic methods. For instance, the puckered, first liquid-permeable layer 21 may be comprised of a spun-bond non-woven fabric having a surface weight of 15 g/m$^2$, while the smooth second liquid-permeable layer 22 may be comprised of a spun-bond non-woven fabric having a surface weight of 20 g/m$^2$. Alternatively, instead of using a smooth, second liquid-permeable layer 22 which is comprised of spun-bond non-woven fabric, said second layer may be comprised of a carded thermobond non-woven fabric having a surface weight of 17 g/m$^2$. It is advantageous to use a spun-bond non-woven fabric as the puckered, first liquid-permeable outer layer, since spun-bond non-woven material can be handled in low surface weights and is felt to be soft against the wearer's skin in use. The non-woven fabrics are essentially inelastic, which is an advantage since this will counteract smoothing of the folds or wrinkles 15 as a result of elastic stretching of the smooth, second liquid-permeable layer 22. The non-woven materials may include for instance polypropylene fibres, polyester fibres, viscose fibres or mixtures thereof. Bicomponent fibres are also conceivable.

As a result of the peaks and troughs of the folds or puckers on the liquid-receiving outer layer 20, the specific liquid-receiving volume of said layer is much greater than the liquid-receiving volume of a conventional liquid-permeable layer having an essentially smooth liquid-receiving surface and therefore a relatively low liquid-receiving volume. This enables liquid to be transported very quickly through the liquid-receiving layer into the absorbent pad. The liquid-receiving outer layer 20 also has a very low re-wetting tendency, i.e. liquid is prevented from passing from the absorbent pad 18 back up through the outer layer 20 and thus from coming into contact with the wearer's skin.

The absorbent material contained by the absorbent pad 18 may be cellulose fluff. The absorbent material may also include liquid-absorbing hydrogels, so-called superabsorbents, by which is meant polymers that are able to absorb liquids in quantities many times their own weight. These hydrogels may be mixed more or less homogeneously in the cellulose fluff or may be placed in layers within the absorbent pad 18. However, the construction of the absorbent pad 18 has no critical significance to the invention, provided that the pad is able to fulfil the requirement of quickly receiving and spreading the liquid that penetrates through the liquid-receiving outer layer 20.

The liquid-impermeable outer layer 19 functions as a barrier layer in preventing leakage of the liquid absorbed by the absorbent pad 18. This liquid-impermeable outer layer 19 may, for instance, be comprised of polyethylene film or like material.

Figure 3:
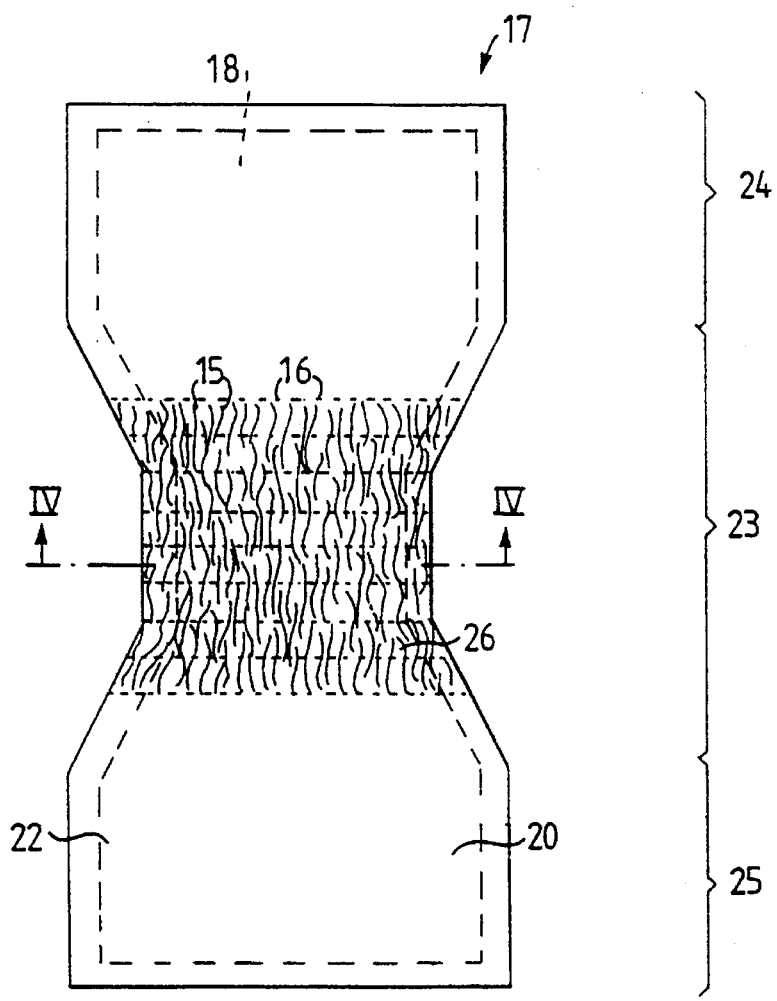
FIG. 3 is a view from above of an incontinence guard according to one embodiment of an inventive absorbent article.
Figure 4:
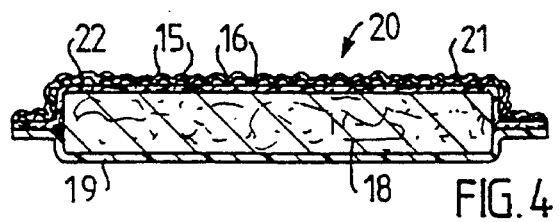
FIG. 4 is a cross-sectional view of the incontinence guard illustrated in FIG. 3.

The puckered, first liquid-permeable layer 21 of the embodiment illustrated in FIG. 3 takes-up an area which is smaller than the total area of the liquid-receiving outer layer 20. The remaining area of the liquid-receiving surface layer 20 is comprised solely of the smooth, second liquid-permeable layer 22. The puckered, first liquid-permeable layer 21 takes-up roughly a third of the surface area of the liquid-receiving outer layer 20 and is placed in the crotch part 23 of the incontinence guard 17, said crotch part being the narrower part of the incontinence guard 17 and is intended to be placed between the wearer's thighs in use. Located on either side of the crotch part 23 is a respective end-part 24, 25 which is intended to face forwardly and rearwardly of the wearer. Since the incontinence guard 17 illustrated in FIG. 3 is fully symmetrical with regard to the configuration of the crotch part 23 and the end-parts 24, 25, there is no actual front and back to the incontinence guard 17. This need not always be the case, however. On the contrary, a diaper, sanitary napkin or an incontinence guard may be provided with a pronounced front and back end so as to achieve the best possible body fit. In this case, the crotch part may be displaced forwardly or rearwardly in the article, according to the intended use of the article and its configuration. Since the crotch part is normally that part of an absorbent article which receives the body liquid excreted by the wearer, the puckered, first liquid-permeable layer 21 will define a liquid-receiving zone 26 in the crotch part 23. Naturally, in certain cases, this liquid-receiving zone 26 may also be located outside the crotch part, for instance in the front part of diapers that are intended for male users, who normally deliver body liquid to a forward part of the diaper located in front of the crotch part. In cases such as these, the puckered, first liquid-permeable layer will, of course, be located in these forward regions of the article. As will be understood, cases are conceivable in which the whole of the liquid-receiving outer layer shall be capable of allowing liquid to pass quickly therethrough and in cases such as these, the puckered, first liquid-permeable layer will cover the whole of the smooth, second liquid-permeable layer. Again, in other cases in which it is desired to save material and not to have a fully covering puckered first layer, two or more puckered layers can be provided which together cover a surface area that is smaller than the whole of the area of the liquid-receiving surface layer but with each layer covering individual parts over more or less separated portions of the incontinence guard. For instance, a plurality of transverse strips may be disposed across the incontinence guard.

The folds 15 illustrated in FIG. 3 are oriented essentially in the longitudinal direction of the incontinence guard 17, although it will be understood that the puckered layer 21 can be applied so that the wrinkles or folds 15 are oriented essentially transversely to the longitudinal direction of the incontinence guard 17. Since the peaks of these folds will, to some extent, prevent liquid and fluid excrement from running transversely to the folds, the direction in which the folds 15 are oriented in different parts of the incontinence guard 17 will also have some significance. It may be beneficial for the folds 15 in the crotch part 17 to extend in the longitudinal direction of the incontinence guard 17, since liquid that meets the liquid-receiving outer layer 20 close to the edge of the incontinence guard will find difficulty in running over the edge of the incontinence guard even if, against expectations, the liquid is not transported quickly through the outer layer 20 and into the absorbent pad 18. Instead, it may be advantageous for the folds or wrinkles in the end-parts 24, 25 to be oriented in the transverse direction of the incontinence guard, at least in the proximity of the end-edges.

It has also been found possible to allow the puckered, first liquid-permeable layer to be turned inwardly towards the absorbent pad without appreciably impairing the short liquid-permeation time, i.e. to permit the smooth layer to receive the liquid first. This may sometimes be preferred for aesthetic reasons, when in the case of certain products it is undesirable for the liquid-receiving outer layer to exhibit a puckered and wrinkled outer surface.

It will be understood that the invention is not restricted to the illustrated exemplifying embodiment thereof and that a number of modifications are conceivable within the scope of the following claims.

I claim:

1. A method for mutually bonding at least two moving continuous material webs to form a laminate having at least one puckered material layer, comprising the following steps:

advancing a first material web from a first depot at a first speed;

advancing a second material web from a second depot at a second speed which is lower than the first speed;

bringing the first material web and the second material web together and mutually bonding said webs together to form the laminate in a web-bonding means while maintaining a difference in speed between the first and the second material webs, wherein the first material web is puckered upon entering the web-bonding means as a result of the higher first speed of the first material web in relation to the second speed of the second material web at a web-bonding moment, whereas the second material web remains essentially smooth; and advancing the laminate from the web-bonding means at a speed which is equal to the lower second speed.

2. The method according to claim 1, wherein a difference between the first speed and the second speed is greater than a contraction rate of the first web at which said first web is deformed solely in its plane without being puckered.

3. The method according to claim 1, wherein the first speed is at least 40% higher than the second speed.

4. The method according to claim 1, wherein when passing through the web-bonding means, the first material web lies against a rotating roll whose peripheral speed is at least equal to the first speed.

5. The method according to claim 1, wherein the webs are mutually bonded by an ultrasonic bonding process.

6. The method according to claim 1, wherein the webs are mutually bonded by a calendaring process, in which a first rotating roll has a peripheral speed which corresponds to the first speed of the first material web, and a second rotating roll has a peripheral speed which corresponds to the second speed of the second material web.

7. The method according to claim 1, wherein the first speed is twice as high as the second speed.

8. An arrangement for mutually bonding at least two moving continuous material webs to form a laminate which includes at least one puckered material layer, comprising:

means for advancing a first material web from a first depot at a first speed;

means for advancing a second material web from a second depot at a second speed which is lower than the first speed;

means for mutually combining the first material web with the second material web;

means for bonding the first material web to the second material web to form the laminate while maintaining a difference in speed between the first material web and, at the same time, to create folds or wrinkles in the first material web as a result of the speed difference while the second material web remains essentially smooth; and means for advancing the laminate from the web-bonding means at the second speed.

9. The arrangement according to claim 8, wherein the web-bonding means (4) includes a rotating roll whose peripheral speed corresponds to the first speed and against which roll the first material web abuts as it passes through the web-bonding means.

10. The arrangement according to claim 9, wherein the web-bonding means includes an ultrasonic horn and said rotating roll, which is comprised of a counterpressure roll that includes a plurality of elements which project out from an outer surface of the roll and which are disposed in a selected pattern and serve as local weld dollies or anvil means in forming welded parts in the laminate, such as to effect bonding of the webs by means of ultrasonic welding.

11. The arrangement according to claim 10, wherein the outwardly projecting elements have the form of a plurality of discrete spikes which are disposed in a discontinuous pattern over at least parts of the outer surface of the counterpressure roll, or of a plurality of separated, elongated ribs placed over at least parts of the outer surface of the counterpressure roll.

* * * * *